United States Patent [19]

Hallett

[11] Patent Number: 5,127,933
[45] Date of Patent: Jul. 7, 1992

[54] COMPLETE FERTILIZER AND FUNGUS NUTRIENT MATERIAL WITH LOW SOLUBILITY AND METHOD FOR MAKING SAME

[76] Inventor: Arne L. Hallett, 285 Maplewood Ave., Bridgeport, Conn. 06605

[21] Appl. No.: 684,778

[22] Filed: Apr. 15, 1991

[51] Int. Cl.$^5$ .................. C05D 11/00; C05C 13/00
[52] U.S. Cl. .................................. 71/5; 71/1; 435/244; 435/254; 47/1.5
[58] Field of Search .......... 71/5, 31, 1; 47/1.5; 435/244, 254

[56] References Cited

U.S. PATENT DOCUMENTS

| | | | |
|---|---|---|---|
| 3,242,237 | 3/1966 | Belak et al. | 71/64.11 |
| 3,574,591 | 4/1971 | Lyons et al. | 71/1 |
| 3,585,020 | 6/1971 | Legal, Jr. et al. | 71/29 |
| 4,549,897 | 10/1985 | Seng et al. | 71/3 |
| 4,789,391 | 12/1988 | Detroit | 71/27 |
| 4,880,455 | 11/1989 | Blank | 71/28 |
| 4,883,530 | 11/1989 | Von Maessenhausen et al. | 71/36 |

*Primary Examiner*—Ferris Lander
*Attorney, Agent, or Firm*—Paul A. Fattibene; Arthur T. Fattibene

[57] ABSTRACT

A complete fertilizer and nutrient material with low solubility comprised of potassium calcium sulfate, calcium ammonium phosphate, and ammonium bitartrate. The low solubility fertilizer is made easily from commonly available substances. Potassium bi-tartrate is dissolved with ammonium hydroxide solution forming a solution. An aqueous slurry is made from calcium sulphate and monocalcium phosphate. The solution and slurry are mixed. A precipitate then forms, which is a complete fertilizer, 8-10-7, having low solubility. The fertilizer is easily produced. The composition can also be used as a nutrient material for growing fungi.

2 Claims, 1 Drawing Sheet

COMPLETE FERTILIZER AND FUNGUS NUTRIENT MATERIAL WITH LOW SOLUBILITY AND METHOD FOR MAKING SAME

FIELD OF THE INVENTION

The present invention relates generally to fertilizer for use in promoting growth in plants, and more particularly to a complete fertilizer with low solubility that is safe and easily produced.

BACKGROUND OF THE INVENTION

It is well known that the controlled release of fertilizer has many advantages. The controlled release of fertilizer prevents "burning." The controlled release fertilizer is also less likely to be washed away. Additionally, more convenient applications are facilitated with a controlled, either slow or limited, release fertilizer due to the need for less frequent and critical applications.

There have been different approaches to providing a controlled release fertilizer. The placement of a coating on the fertilizer is one such solution. Various coatings have been used, such as those disclosed in U.S. Pat. No. 4,549,897 issuing to Seng et al on Oct. 29, 1985 and entitled "Protein Degraded Pre-Vulcanized Natural Rubber Coated Slow Release Fertilizers", and U.S. Pat. No. 4,880,455 issuing to Blank on Nov. 14, 1989 and entitled "Method for the Manufacture of Slow Release Fertilizers". Yet another approach is to provide substances that act as a fertilizer that have relatively low levels of solubility. One example of such a fertilizer is disclosed in U.S. Pat. No. 3,574,591 issuing to Lyons et al on Apr. 13, 1971 and entitled "Methods for Preparing Mixed Cation Polyphosphates". Therein disclosed is a fertilizer composition of mixed cation polyphosphates with reduced solubility.

There is a need for an easily prepared complete fertilizer that has controlled release due to low solubility.

SUMMARY OF THE INVENTION

The present invention is directed to a complete fertilizer with low solubility having a composition of potassium calcium sulfate, calcium ammonium phosphate, and ammonium bitartrate. The low solubility complete fertilizer is formed by making a solution of potassium bitartrate and ammonium hydroxide. This solution is then mixed with a slurry of calcium sulfate and monocalcium phosphate. The solution and slurry, when mixed, produce a precipitate which forms the fertilizer, with much lowered solubility, of the present invention. The fertilizer can be made simply from easily obtainable ingredients to result in an intimate mixture of unusual compounds.

Accordingly, it is the primary object of the present invention to provide a complete fertilizer with low solubility.

It is an advantage of the present invention that it can be produced with commonly available compounds to result in a combination of uncommon compounds with a good balance of nutrients, and a more useful and safer level of solubility.

It is a feature of the present invention that less critical fertilizer applications can be achieved without damage to plants.

Because of low solubility, the fertilizer is generally safe for plants when used in any quantity.

These and other objects, advantages, and features will become readily apparent in view of the following more detailed description.

DETAILED DESCRIPTION OF THE PREFERRED EMBODIMENT

Figure 1:
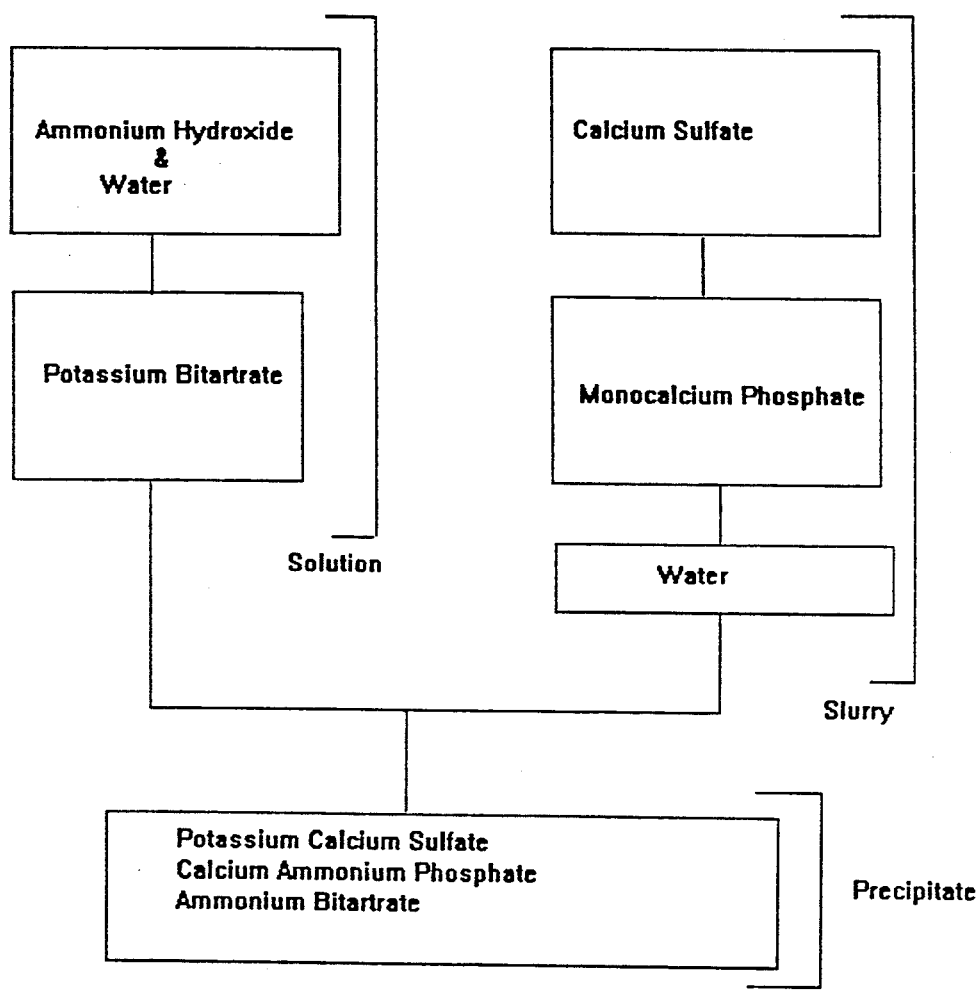
FIG. 1 is a flow chart illustrating a method of making the fertilizer of the present invention.

FIG. 1 illustrates one method by which the low solubility complete fertilizer of the present invention can be produced. As can clearly be seen in FIG. 1, potassium bitartrate ($KHC_4H_4O_6$), also known by the common name cream of tartar, is mixed with ammonium hydroxide solution ($NH_4OH$) $H_2O$ to form a solution. A slurry is then formed by combining calcium sulfate ($CaSO_4$) with monocalcium phosphate ($Ca(H_2PO_4)_2$), and some added water ($H_2O$).

The solution and slurry are then mixed. A precipitate is formed, comprised of potassium calcium sulfate ($K_2Ca(SO_4)_2$), calcium ammonium phosphate ($NH_4CaPO_4$), and ammonium bitartrate ($NH_4HC_4H_2O_6$). This precipitate is a complete fertilizer with low solubility. This fertilizer can be produced very easily using commonly available ingredients.

A small quantity of low solubility fertilizer has been produced according to the present invention by combining approximately one pint of a 10% solution of ammonium hydroxide with approximately 4.3 ounces by weight of cream of tartar to form a solution. This solution was then mixed with a slurry comprised of approximately 3.3 ounces by weight of plaster of paris and approximately 2.9 ounces by weight of monocalcium phosphate together with a small quantity of water sufficient to form a slurry. When the solution and slurry are combined, a precipitate is formed that when separated and dried, forms the complete fertilizer with a lowered level of solubility consisting essentially of potassium calcium sulfate, calcium ammonium phosphate, and ammonium bitartrate.

The composition of the present invention is very tolerant to impurities. In fact, the expected impurities will be beneficial to plant growth and health. Ingredients of varying degrees of purity may therefore be used, such as argols, super phosphate, triple super phosphate, gypsum, and plaster of paris. The weights should be adjusted accordingly.

The formula to be used to produce the low solubility fertilizer of the present invention is as follows:

$$4[NH_4OH] + 2[KHC_4H_4O_6] + 2[CaSO_4 \cdot 1/2H_2O] + CaH_4(PO_4)_2 \cdot H_2O + 9H_2O \rightarrow K_2Ca(SO_4)_2 \cdot H_2O + 2[NH_4CaPO_4 \cdot 7H_2O] + 2[NH_4HC_4H_4O_6].$$

The intermediate steps in the chemical rearrangement in the above formula and process is as follows:
1. $4(NH_4OH) + 2(KHC_4H_4O_6) \rightarrow 2(NH_4HC_4H_4O_6) + 2(NH_4OH) + 2(KOH)$
2. $2(KOH) + 2(CaSO_4 \cdot 1/2H_2O) \rightarrow K_2Ca(SO_4)_2 \cdot H_2O + CaOH + OH$
3. $CaOH + OH + CaH_4(PO_4)_2H_2O + 2(NH_4OH) + 9H_2O \rightarrow 2(NH_4CaPO_4 \cdot 7H_2O)$ The resulting fertilizer is a complete fertilizer, that is it contains nitrogen, phosphorous, potassium, and certain other elements. The contents of a complete fertilizer are generally indicated by three numbers indicating the percentage of each element in standardized form. Therefore, an 8-10-7 fertilizer will contain 8% nitrogen, 10% phosphoric acid, and 7% potash. The present invention when prepared according to the above formula is a complete fertilizer with the proportions of 8-10-7. Additionally, the present fertilizer promotes a deep green growth in plants.

Once produced, the fertilizer of the present invention should preferably be packed in glass jars and sealed. If exposed to air, the fertilizer will support limited fungal growth. Fungal growth can be avoided by including a fungus inhibitor. However, in most instances, this will not be necessary in order to get good results from the use of the fertilizer.

The present invention can also be used to purposely and selectively encourage fungal growth in some applications. Therefore, the present invention is also useful as a nutrient for fungal growth. In such applications the tartaric acid and/or its compounds, as in the present invention, acts as the organic energy nutrient. This replaces other organic energy nutrients, such as carbohydrates.

While the fertilizer may be applied in the form of a powder, it could also be processed into pellets or tablets, either coated or uncoated. Pellets, in some applications, may be more easily handled.

Although the preferred embodiment has been illustrated and described, it will be obvious to those skilled in the art that various modifications may be made without departing from the spirit and scope of this invention.

What is claimed:

1. A process for encouraging fungus growth comprising the step of:
   using as a growth nutrient the following $K_2Ca(SO_4)_2 \cdot H_2O^* + 2[NH_4CaPO_4 \cdot 7H_2)] + 2[NH_4HC_4H_4O_6]$.

2. A low solubility complete fertilizer made according to the following formula:

$$4[NH_4OH] + 2[KHC_4H_4O_6] + 2[CaSO_4 \cdot \tfrac{1}{2}H_2O] + CaH_4(PO_4)_2 \cdot H_2O + 9H_2O$$
$$\rightarrow K_2Ca(SO_4)_2 \cdot H_2O + 2]NH_4CaPO_4 \cdot 7H_2O] + 2[NH_4HC_4H_4O_6],$$

wherein the precipitated product of $K_2Ca(SO_4)_2 \cdot H_2O + 2[NH_4CaPO_4 \cdot 7H_2O] + 2[NH_4HC_4H_4O_6]$ forms the low solubility complete fertilizer.

* * * * *